US00PP27904P2

(12) United States Plant Patent
Hansen

(10) Patent No.: US PP27,904 P2
(45) Date of Patent: Apr. 18, 2017

(54) ***BAPTISIA* PLANT NAMED 'SPARKLING SAPPHIRES'**

(50) Latin Name: ***Baptisia* hybrid**
Varietal Denomination: Sparkling Sapphires

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 7 days.

(21) Appl. No.: 14/757,104

(22) Filed: Nov. 19, 2015

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

A new and distinct plant cultivar of hardy herbaceous false indigo named *Baptisia* 'Sparkling Sapphires' characterized by compact mound-shaped habit with highly-branched upright stems and many large, intense blue-colored flowers held above the foliage in the late spring, suitable for landscaping as a specimen or en masse.

1 Drawing Sheet

Botanical classification: *Baptisia* hybrid.
Cultivar designation: 'Sparkling Sapphires'.

BACKGROUND OF THE INVENTION

The present invention relates to a new and distinct cultivar of hybrid *Baptisia* plant, botanically known as *Baptisia* 'Sparkling Sapphires' and will be referred to hereafter by its cultivar name, 'Sparkling Sapphires'. The new cultivar represents a new false indigo plant, a long-lived, hardy, herbaceous perennial grown for landscape and cut flower use.

The new invention arose from an ongoing breeding program at a nursery in Waseca, Minn. and continued at a wholesale perennial nursery in Zeeland, Mich. with the specific intention of improving garden worthiness of perennial False Indigo plants with a wider variety of flower colors and improved garden habit.

Open pollinated seed was collected by the hybridizer from the proprietary unreleased *Baptisia sphaerocarpa* 'Linda' (not patented) the inventor in September of 2009. The new individual plant was a single seedling assigned the breeder code H9-49-01 and was approved for final selection in spring of 2013 in Zeeland, Mich. The male or pollen parent may have come from any one of a number of named or unreleased hybrids within a vast group in the breeding fields in Waseca, Minn., but because of the resultant traits of the new plant it is presumed the male parent was of *Baptisia minor* background.

No plants have been sold, either in this country or anywhere in the world, prior to the filing of this application, nor has any disclosure been made prior to the filing of this application with the exception of that which was within one year of the filing of this application and was derived directly or indirectly from the inventor.

Compared to the female parent the new plant is more compact, better branched and has more intense blue flowers, rather than the yellow flowers of 'Linda'. The new plant produces fruit that is more elliptic and less globose than 'Linda'. 'Linda' has stems about 115 cm tall that are less upright producing a plant nearly 150 cm across compared to the 85 cm height and 78 cm width of the new plant.

The nearest comparison variety is 'Blue Bonnet' (not patented) which is slightly shorter in habit with flowers that are not as intense blue and more separated on the stem. Compared to other similar plants, 'Blueberry Sundae' U.S. Plant Pat. No. 23,891 is more lavender purple in color and has lighter intensity. *Baptisia* 'Midnight' U.S. Plant Pat. No. 20,432 is much taller and more vase shaped. Compared to 'Blue Mound' U.S. Plant Pat. No. 25,902 the new plant is shorter, has longer peduncles with more flowers and more intense blue flowers.

*Baptisia* 'Sparkling Sapphires' differs from all cultivars known to the inventor in the following combined traits:

1. Compact mounded habit with upright highly-branching stems;
2. Many large, intense blue-colored flowers on well-branched stems held above the foliage in the spring;
3. Branches and foliage develop in summer to produce rounded habit and cover base of inflorescences.

BRIEF DESCRIPTION OF THE DRAWINGS

The photographs of the new plant demonstrate the unique traits of the new plant and the overall appearance. The colors are as accurate as reasonably possible with color reproductions. Variation in ambient light spectrum, source and direction may cause the appearance of minor variation in color. The accompanying photograph is of a three-year old plant growing in an open full-sun trial garden in Zeeland, Mich.

DETAILED BOTANICAL DESCRIPTION OF THE PLANT

Figure 1:
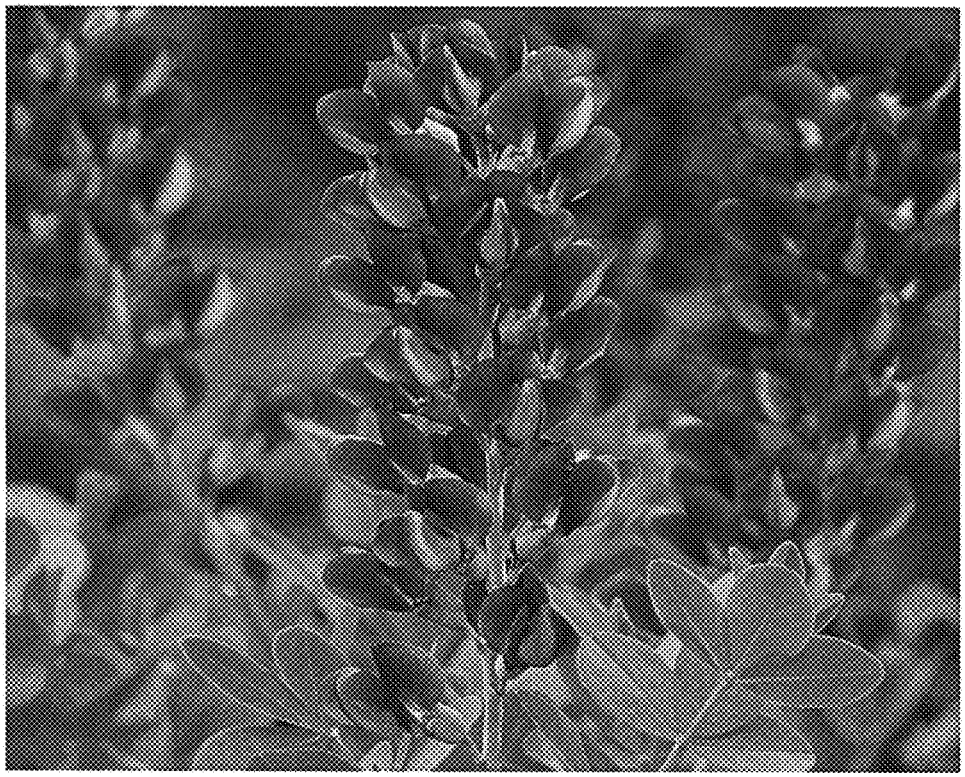
FIG. 1 shows a close-up of the flower scape.
Figure 2:
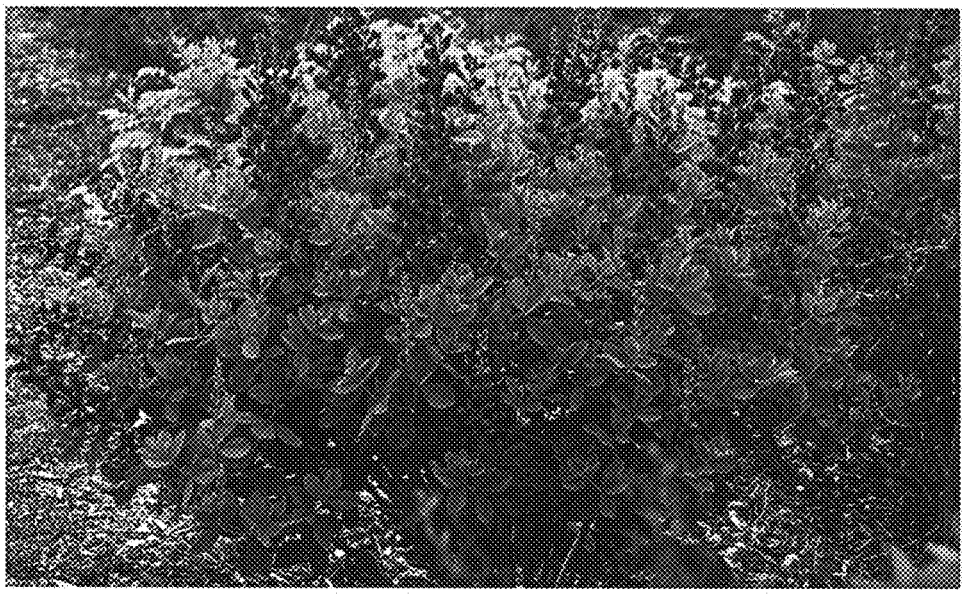
FIG. 2 shows the habit of a plant in full flower.

The following is a detailed description of five-year-old plants of the new cultivar as grown outdoors in a trial plot at a wholesale nursery in Zeeland, Mich. Plants of the new cultivar have not been tested under all possible conditions.

The phenotype may vary with changes in environment, climate, and cultural conditions without change however in the genotype. The color reference is in accordance with the 2001 edition of The Royal Horticultural Society Colour Chart except where general color dictionary terms are used.

Plant habit: Perennial, compact, well-branched, many-stemmed, mounded growth habit with many-flowered inflorescences held above the foliage.

Plant size: Average about 85 cm tall and 80 cm wide about 45 cm above soil.

Roots: Fibrous, well-branched, long, deeply rooted.

Root color: Nearest RHS 161D depending on soil type.

Growth and propagation:

*Propagation method*.—Stem cuttings, rooting in about three weeks.

*Growth rate*.—Moderately, similar to other *Baptisia*.

Stems: Rigid and upright; glaucous; glabrous; cylindrical with longitudinal ridges and furrows; flexuose at branched nodes; lower two nodes without leaves or branches; normally about 18 to 24 stems per plant; main stem to about 10.0 mm diameter at base and to about 85.0 cm tall to top of inflorescence, average about 80.0 cm tall and about 7.0 mm diameter; normally about five alternately-arranged primary branches at 45° to 55° angle above horizontal; lower branches up to about 40.0 cm long to end of inflorescence and about 8.0 mm diameter at base, average for primary branches about 34.0 cm long and about 7.0 mm diameter, smaller distally; four alternately-arranged secondary branches per stem up to about 24.0 cm long and 2.5 cm diameter; frequently four alternately-arranged tertiary branches up to about 16.0 cm long and 1.5 mm diameter with some lower tertiary branching having two to four quaternary branches up to about 12.0 cm long and 1.0 mm diameter at base; foliage of combined branches extending to about 65 cm above soil.

Stem color: Nearest RHS 138B.

Stem scales: At lower stem nodes; acute to frequently emarginated apex with truncate base; rapidly dehiscing to leave behind thin scar; about 18.0 mm long and 12.0 mm wide at base; color nearest RHS 202A.

Internodes: Up to about 11.5 cm apart between lowest nodes, average about 8.2 cm; color same as surrounding stem.

Foliage: Elliptic, acute apex, acute base; to about 30 mm long and 20 mm wide in center; alternate on stem; ternate to palmately compound with three leaflets; outer two leaflets at about 80 degree angle to middle leaflet.

Leaflet: Three, elliptic, acute apex, attenuate base; margins entire; glabrous; top surface matte, scaberulose below; size up to 5.0 cm long and 2.4 cm wide, average about 3.2 cm long and 1.8 cm wide.

Leaflet color: Newly expanding between RHS N144D and RHS N144C on upper and lower surfaces; mature adaxial surface between RHS N138B and RHS 138A; mature abaxial nearest RHS N138D.

Venation: Reticulate; adaxial glabrous, glaucous, thin, not conspicuous; abaxial conspicuous.

Vein color: Adaxial between RHS N144D and RHS N144C and abaxial between RHS 138B and RHS 139B; main center vein nearest RHS 143C above lighter than RHS 138D below.

Petioles: Glabrous; glaucous; clasping; concaved facing upward; up to about 3.0 mm long and 2.0 mm wide average 2.5 mm long and 2.0 mm wide.

Petiole color: Nearest 138C on upper and lower surfaces.

Stipules: Lanceolate, acute apex with base truncate to stem; up to 1.5 cm long and 6 mm wide, average 1.0 cm long and 4.0 mm wide with largest stipules below primary branches and decreasing distally and on secondary branches.

Stipule color: Nearest RHS 138C both surfaces.

Flower: Zygomorphic, papilionaceous, non-secund, held at about 50° angle above horizontal; beginning about 53 cm above soil; up to about 55 flowers per main raceme and about 25 per secondary branch; seasonally effective for about 3 to 4 weeks beginning in late May in Zeeland, Mich. with about 30 flowers and 15 buds showing color during peak; individual flower remain effective and on raceme for about four days; individually about 2.6 cm long, 1.7 cm tall and 1.4 cm wide at tallest and widest portions; an upper banner, a lower keel made up of two lobes folded around gynoecium and androecium; and two lateral wings or alae laterally appressed against keel.

Flower fragrance: None detected.

Peduncle: Rounded with vertical ridges and furrows; glaucous; glabrous; from first flower to apex about 32 cm long; diameter at the base of first flower about 5.0 mm and about 1.0 mm diameter at the apex.

Peduncle color: Between RHS N138D and RHS 139D with light tinting of nearest RHS N187B in upper portions or where exposed to more light.

Pedicel: Round, glabrous, glaucous; about 10.0 mm long and 1.0 mm diameter.

Pedicel color: Proximally nearest RHS 146D; distally and on young unopened flowers nearest RHS 146D with light tinting of RHS N187A.

Calyx: Campanulate, about 11.0 mm long and 7.0 mm across at opening; five-lobed with top lobe dissected about 2.0 mm deep; apex obtuse, basal two thirds fused; margins entire; slightly glaucous; persists after petal drop.

Calyx color: Between RHS 146D and RHS 138A with slight tinting toward calyx apex and distal regions exposed to more intense sunlight nearest RHS N187B; distal one-half and calyx on unopened buds developing tinting of nearest RHS N187B.

Buds one day prior to anthesis: Oblong reniform, flatted vertically; about 2.2 cm long and 8.0 mm tall and 5.0 mm wide.

Bud color: One day prior to opening keel petal lower center section lighter than RHS155D; banner petal between RHS N92C and RHS 92D.

Petals: Five; with a lower fused keel, an upper banner, and two lateral wings or alae; keel comprised of two sections that are folded around stamens and pistil.

*Banner petal*.—Conduplicate, curved upward and backward and pinched in the middle; apex retuse, base claw-like; about 2.2 cm long, 1.4 cm across at widest and 7.4 mm tall; banner dorsal side color between RHS N92D and RHS N92C at perimeter with the inner center portion between RHS N92B and RHS N92C, ventral side nearest between RHS N92D and RHS N92C; both sides of claw portion lighter than RHS 155D with basal tinting of between RHS 150D and RHS 145D.

*Keel*.—Comprised of two main lobes that are folded around stamens and pistil; fused along the margin in the distal one-third with the apex emarginate to retuse and the bases separate and claw-like; top margin about 5.0 mm from base has 2.0 mm smaller lobe pointing toward base; about 26.0 mm long 1.5 mm across and 9.0 mm tall with claw base narrowed to 2.0 mm wide for the proximal 4.0 mm; color of outer and inner keel sides between RHS N92D and RHS N92C with basal 6.0 mm lighter than RHS 155D; claws nearest RHS 155C.

*Alae*.—Papilionaceous corolla appendage with rounded apex and claw-like base; with 2.0 mm lobe pointing toward base and about 5.0 mm from base; about 21.0 mm long and 9.5 mm tall with the claw narrowed to 2.0 mm wide for the proximal 5.0 mm; alae outside color nearest RHS 155D with the distal margin intensifying in the outer 1.0 to 3.0 mm to nearest RHS 83A; color inside nearest RHS 155D with the distal margin intensifying in the outer 1.0 mm to nearest RHS 83A; claw nearest RHS 155D on both surfaces.

Receptacle: Disk-shaped, about 3.5 mm diameter and 1.2 mm depth; color nearest RHS N144D.

Gynoecium: One, with superior ovary.

*Pistil*.—About 19.0 mm long and 1.5 mm wide; color nearest RHS 143C.

*Style*.—Slightly arcuate; glabrous; about 9.0 mm long and less than 1.0 mm diameter; color nearest RHS N144B.

*Stigma*.—Less than 0.5 mm diameter; color between RHS 145A and RHS 145B.

*Ovary*.—Superior suspended by stipe; about 7.0 mm long and about 1.5 mm in diameter; color nearest RHS 144A.

*Stipe*.—About 3.5 mm long and 1.0 mm diameter; color nearest RHS N144D.

Androecium:

*Stamens*.—Ten, not united, about 20.0 mm long and about 1.0 mm diameter.

*Filament*.—1.9 cm in length and less than 1 mm in diameter; curved about 30° in about terminal 7.0 mm; filament color between RHS 145 D and RHS 145C; lighter at apex and darker at base.

*Anther*.—Dorsifixed, longitudinal, oblong; about 2.0 mm long and about 1.0 mm wide; color nearest RHS N186B.

*Pollen*.—Spherical; abundant; color nearest RHS 17A.

Fruit: Mono-carpellate, septicidal capsule; elliptic, with arcuate mucro about 10.0 mm long and rounded to attenuate base; about 2.5 cm long without mucro and about 1.0 cm diameter; color at maturity nearest RHS N200A outside and nearest RHS N199A inside.

Seed: Reniform, compressed side to side, about 3.2 mm long, 1.5 mm thick and 2.2 mm across; normally about 3 per fruit (open-pollinated); color between RHS 165A and RHS N199C.

Hardiness: To USDA zones 4 to 8; heavy clay or light loamy sand soils; able to withstand drought conditions once established.

Diseases: Susceptibility or resistance to diseases beyond that typically found in other false indigo plants has not been observed.

I claim:

1. A new and distinct plant cultivar of hardy herbaceous false indigo named *Baptisia* 'Sparkling Sapphires' as herein described and illustrated.

* * * * *